United States Patent
Martin (10) Patent No.: US 12,076,156 B2
(45) Date of Patent: Sep. 3, 2024

(54) ALLERGY TESTING DEVICE

(71) Applicant: Parker Ray Martin, Ann Arbor, MI (US)

(72) Inventor: Parker Ray Martin, Ann Arbor, MI (US)

(*) Notice: Subject to any disclaimer, the term of this patent is extended or adjusted under 35 U.S.C. 154(b) by 639 days.

(21) Appl. No.: 17/214,847

(22) Filed: Mar. 27, 2021

(65) Prior Publication Data
US 2021/0315510 A1    Oct. 14, 2021

Related U.S. Application Data (60) Provisional application No. 63/007,363, filed on Apr. 8, 2020.

(51) Int. Cl.
   A61B 5/00    (2006.01)

(52) U.S. Cl.
   CPC .............. *A61B 5/411* (2013.01); *A61B 5/004* (2013.01); *A61B 5/445* (2013.01); *A61B 5/742* (2013.01); *A61B 2560/0406* (2013.01)

(58) Field of Classification Search
   CPC ......... A61B 5/411; A61B 5/004; A61B 5/445; A61B 5/742; A61B 2560/0406; A61B 5/0077
   See application file for complete search history.

(56) References Cited

U.S. PATENT DOCUMENTS

| | | | |
|---|---|---|---|
| 5,099,857 A | 3/1992 | Baldo et al. | |
| 10,455,137 B2 | 10/2019 | Saphier et al. | |
| 2002/0016539 A1 | 2/2002 | Michaelis et al. | |
| 2004/0176701 A1 | 9/2004 | Fujii | |
| 2005/0171480 A1 | 8/2005 | Mukerjee et al. | |
| 2011/0270122 A1* | 11/2011 | Mir | A61M 37/0015 600/556 |
| 2016/0058377 A1 | 3/2016 | Butte et al. | |
| 2017/0245792 A1* | 8/2017 | Tversky | A61B 5/445 |
| 2017/0347938 A1 | 12/2017 | Mena Benito et al. | |
| 2018/0249942 A1* | 9/2018 | Bachert | A61B 5/6849 |
| 2021/0169396 A1* | 6/2021 | Stepien | A61B 5/445 |

FOREIGN PATENT DOCUMENTS

CO    20180007546 A1    1/2020

\* cited by examiner

*Primary Examiner* — May A Abouelela
*Assistant Examiner* — Yasmeen S Warsi
(74) *Attorney, Agent, or Firm* — Varnum LLP (57) ABSTRACT

An allergy testing device is disclosed. The allergy testing device includes a first applicator, a second applicator, a capture device, and a processor. The first applicator is arranged to apply an allergen to a first predetermined area of a patient's skin. The second applicator is arranged to apply antigen epitopes within a second predetermined area of a patient's skin. The capture device has a projector and one or more cameras. The processor is in communication with the capture device and a drive device that is arranged to move the first applicator to apply the allergen to the patient's skin and to move the second applicator to apply antigen epitopes to the patient's skin.

3 Claims, 6 Drawing Sheets

ALLERGY TESTING DEVICE

CROSS-REFERENCE TO RELATED APPLICATION

The present application claims the benefit under 35 U.S.C. § 119(e) of U.S. Provisional Application Ser. No. 63/007,363, filed Apr. 8, 2020, which is incorporated herein by reference in the entirety.

TECHNICAL FIELD

The present disclosure relates to an allergy testing device.

BACKGROUND

Current testing for IgE mediated allergic reactions is a time intensive prospect requiring trained professionals for accurate administration and interpretation of test results. Frequently, patients have allergic reactions to a number of allergens including, but not limited to, food, environmental, or drug allergens which can trigger unpleasant or dangerous reactions upon exposure to the patient's immune system. The prevalence of some allergies appears to be increasing while others appear to be over diagnosed, leading to a challenging dilemma requiring clinicians to weigh caution against the negative effects of allergen avoidance.

Traditional allergy testing requires lengthy visits to a specialist's office where a test can be applied and interpreted by a trained professional. This is a time-consuming process which is prone to human error. Access to allergy testing is limited in many settings and is often not available in a timely fashion despite increased patient morbidity and mortality associated with unknown or misdiagnosed allergies. Presently there is no offering of a reliable, automated administration and interpretation of allergy testing.

Therefore, it would be desirable to provide a system and method that cure one or more shortfalls of the previous approaches identified above.

SUMMARY

An allergy testing device is disclosed, in accordance with one or more embodiments of the present disclosure. In one embodiment, the allergy testing device includes a first applicator, a drive device, a capture device, and a processor. The first applicator is connected to a housing. The drive device is connected to the housing and is arranged to move the first applicator between a first applicator first position and a first applicator second position. The capture device is connected to the housing and is spaced apart from the first applicator. The processor is programmed to operate the capture device to project a first predetermined set/series of patterns onto the patient's skin within the first and/or second predetermined area; operate the capture device to capture a first set/series of images of a first and/or second predetermined area of a patient's skin; and operate the drive device to move the first applicator from the first applicator first position towards the first applicator second position, within the first predetermined area.

An allergy testing device is disclosed, in accordance with one or more embodiments of the present disclosure. In one embodiment, the allergy testing device includes a first applicator, a second applicator, a capture device, and a processor. The first applicator is arranged to apply an allergen to a first predetermined area of a patient's skin. The second applicator is arranged to apply antigen epitopes within a second predetermined area of a patient's skin. The capture device has a projector and one or more cameras. The processor is in communication with the capture device and a drive device that is arranged to move the first applicator to apply the allergen to the patient's skin and to move the second applicator to apply antigen epitopes to the patient's skin.

A method of allergy testing is disclosed, in accordance with one or more embodiments of the present disclosure. In one embodiment, the method includes capturing a first image set/series of a first and/or second predetermined area of a patient's skin and applying an allergen within the first predetermined area of the patient's skin. After a first predetermined time period, the method further includes capturing a second image set/series of the first predetermined area of the patient's skin and determining a significance of the second image set/series. Responsive to the determination derived from the second image set/series being considered significant, the method further includes outputting for display a first indicator indicative of an allergic reaction.

It is to be understood that both the foregoing general description and the following detailed description are exemplary and explanatory only and are not necessarily restrictive of the present disclosure as claimed. The accompanying drawings, which are incorporated in and constitute a part of the specification, illustrate embodiments of the present disclosure and together with the general description, serve to explain the principles of the present disclosure.

BRIEF DESCRIPTION OF THE DRAWINGS

The numerous advantages of the disclosure may be better understood by those skilled in the art by reference to the accompanying figures.

DETAILED DESCRIPTION

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure. Reference will now be made in detail to the subject matter disclosed, which is illustrated in the accompanying drawings.

Figure 1:
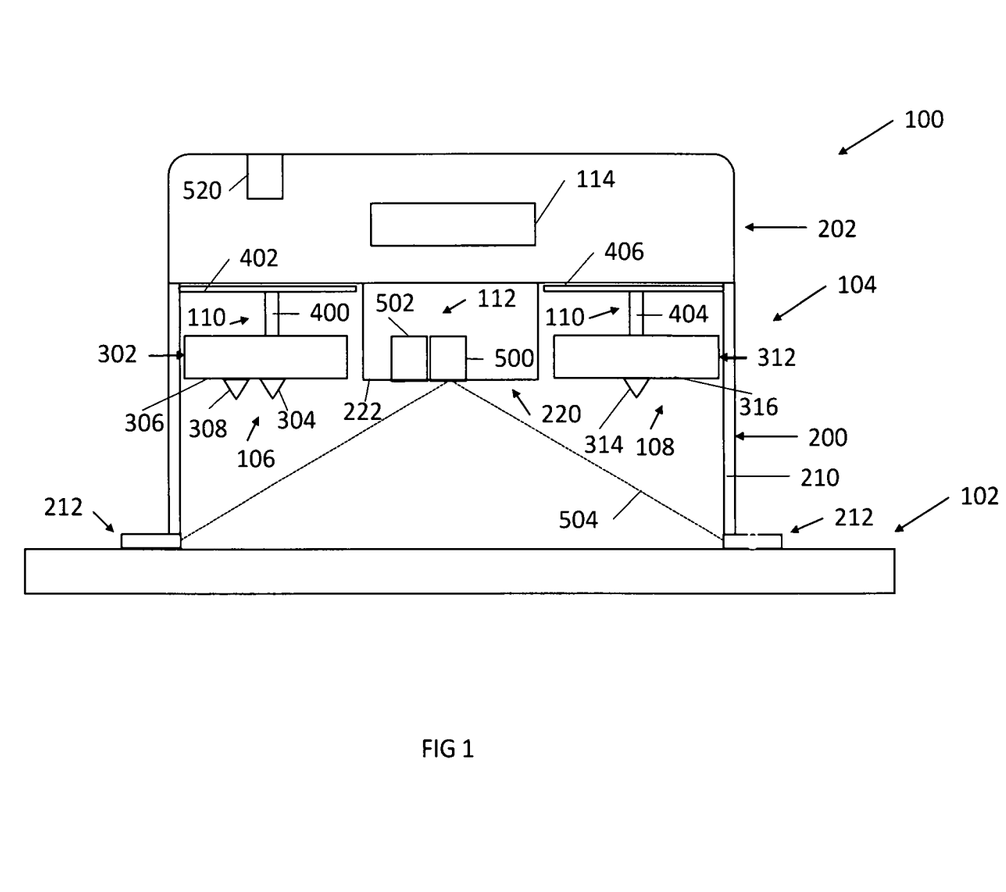
FIG. 1 is a simplified schematic view of an allergy testing device, in accordance with one or more embodiments of the present disclosure.
Figure 4:
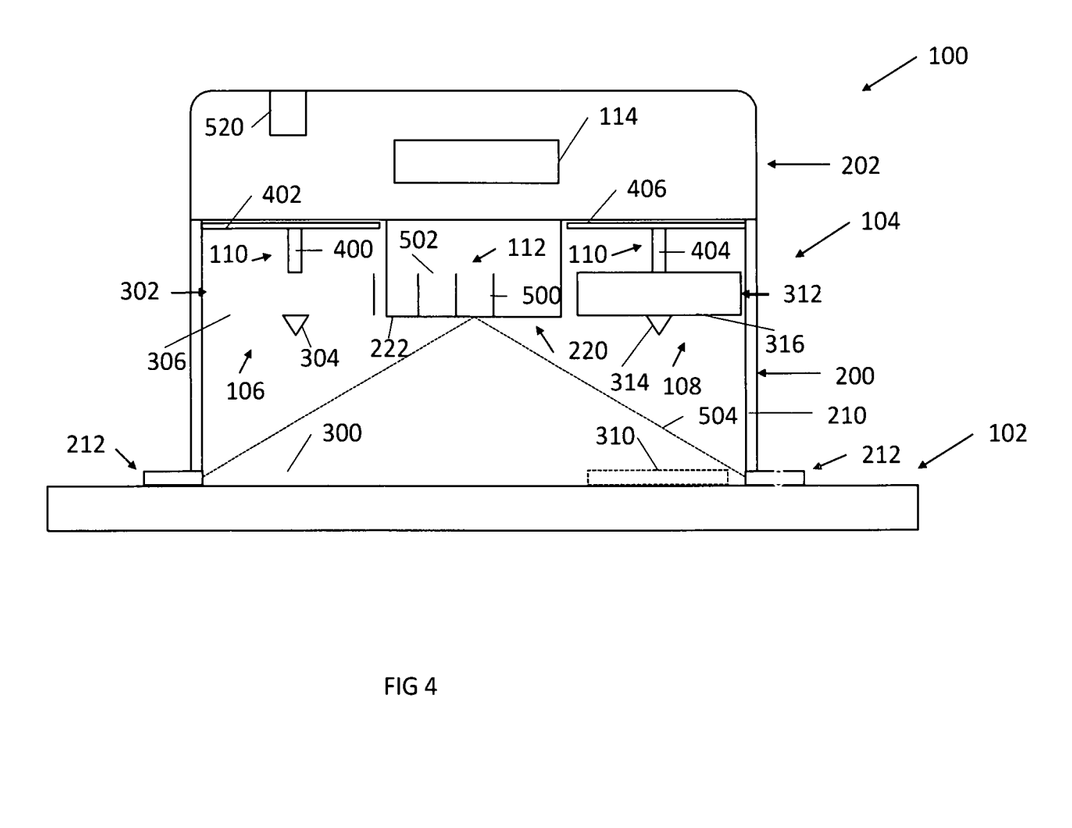
FIG. 4 is a simplified schematic view of the allergy testing device in a first position or retracted position.
Figure 5:
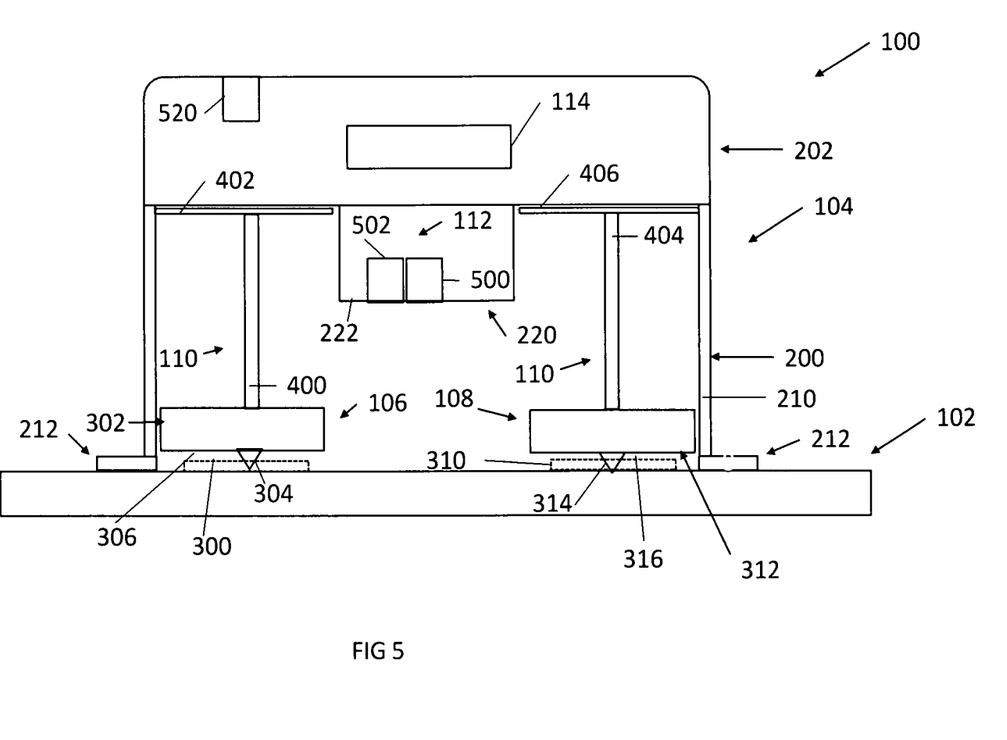
FIG. 5 is a simplified schematic view of the allergy testing device in a second position or extended position.

Referring generally to FIGS. 1, 4, and 5, an allergy testing device 100 is illustrated in accordance with one or more embodiments of the present disclosure. The allergy testing device 100 is arranged to both apply an allergy test to a patient's skin 102 as well as interpret and report the results of this test. The allergy testing device 100 includes a housing 104, a first applicator 106, a second applicator 108, a drive device 110, a capture device 112, and at least one processor 114.

The housing 104 may include a first housing member 200 and a second housing member 202. The first housing member 200 and the second housing member 202 may be joined together such that they are of unibody construction. The first housing member 200 and the second housing member 202 may be joined to each other such that the second housing member 202 is removable or separable from the first housing member 200. In at least one embodiment, at least a portion of the first housing member 200 may be movable relative to the second housing member 202 due to the operation of the drive device 110.

The first housing member 200 defines a wall 210. The wall 210 extends between a portion of the second housing member 202 and a securing device 212 that engages the patient's skin 102. The wall 210 is disposed about and receives portions of the first applicator 106, the second applicator 108, and the capture device 112. The first housing member 200 may be referred to as a lower unit or reservoir unit.

The wall 210 serves multiple purposes including spacing the capture device 112 a predetermined distance from the patient's skin 102 and inhibits ambient or external light intrusion into a chamber or space defined by the inner surface of the wall 210 and the second housing member 202. As such, the wall 210 of the first housing member 200 may be constructed of an opaque or non-transparent material.

The securing device 212 may be disposed at a distal end of the wall 210 of the first housing member 200. The securing device 212 may be an adhesive pad that engages the patient skin 102 to resist or inhibit movement of the allergy testing device 100 relative to the patient's skin 102. The securing device 212 may be removable from the wall 210 such that it may be discarded after the allergy testing device 100 has been disconnected from the patient's skin 102 at the conclusion of an allergy test.

In at least one embodiment, the securing device 212 may be operatively connected to at least one of the first housing member 200 and the second housing member 202. In such an embodiment, the securing device 212 may be a strap, band, or the like that extends about or extends from at least one of the first housing member 200 and/or the second housing member 202 and extends about a portion of a body part of the patient, such as an arm. In such an embodiment, a distal end of the wall 210 that is disposed opposite the second housing member 202 may engage or be disposed proximate the patient's skin 102.

The second housing member 202 is spaced apart from the patient's skin 102 by the wall 210 of the first housing member 200. The second housing member 202 is disposed about or is arranged to receive the drive device 110, the capture device 112, and the processor 114. The second housing member 202 may be referred to as a technology unit.

The second housing member 202 includes a protrusion 220 that is arranged to extend towards the patient's skin 102. The protrusion 220 is disposed between the first applicator 106 and the second applicator 108. The wall 210 is disposed about the protrusion 220.

The protrusion 220 defines a shelf 222 that is disposed generally parallel to the patient's skin 102 and is disposed generally perpendicular to the wall 210 of the first housing member 200. The wall 210 of the first housing member 200 is arranged to space the shelf 222 a predetermined distance from the patient's skin 102. The shelf 222 may be the lowest point of the second housing member 202.

The first applicator 106 and the second applicator 108 are at least partially disposed within the first housing member 200. The first applicator 106 and the second applicator 108 are operatively connected to at least one of the first housing member 200 or the second housing member 202 of the housing 104. In the embodiment shown, the first applicator 106 and the second applicator 108 are connected to the second housing member 202 and are arranged to move relative to the first housing member 200.

In some embodiments, the first applicator 106 and the second applicator 108 may be disposed proximate the distal end of the wall 210 of the first housing member 200. In such an embodiment, a portion of the first applicator 106 and the second applicator 108 may extend beyond the distal end of the wall 210 of the first housing member 200 such that operation of the drive device 110 may move the first housing member 200 or the first applicator 106 and the second applicator 108 relative to the second housing member 202 to apply allergens or the like to a patient's skin 102.

Figure 2:
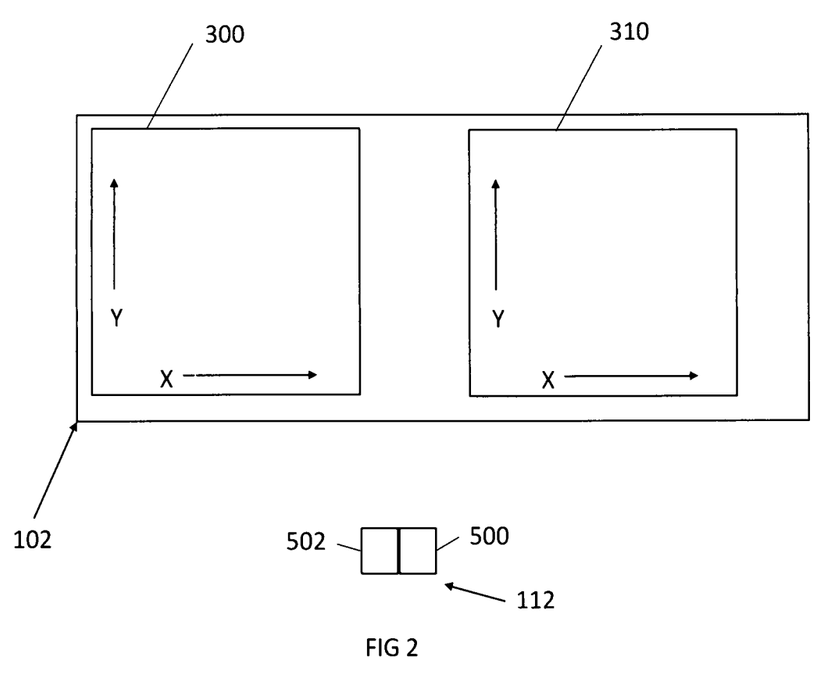
FIG. 2 is a view of first and second predetermined areas on a patient's skin.
Figure 3:
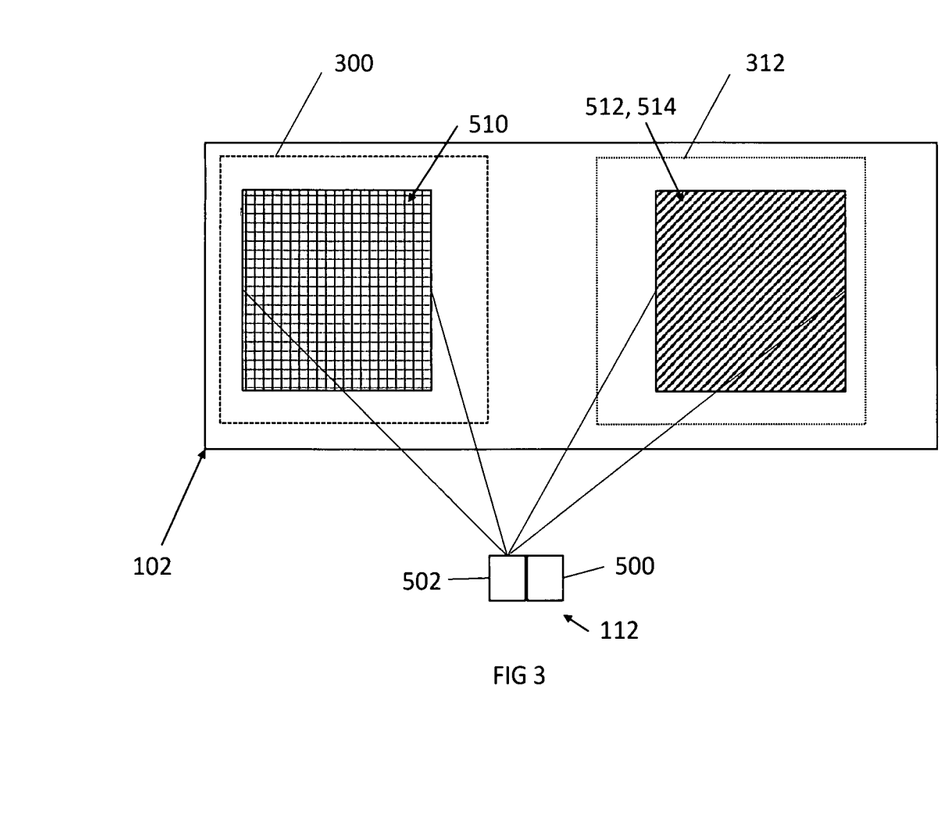
FIG. 3 is a view of first and second predetermined patterns projected onto the first and second predetermined areas.

The first applicator 106 is arranged to apply an allergen or the like to a first predetermined area 300 of the patient's skin 102, as shown in FIGS. 2, 3, and 5. A footprint of or a cross sectional area of the first applicator 106 may be equal to or less than the first predetermined area 300.

The first applicator 106 includes a reservoir 302 and a prong or a needle 304. The reservoir 302 contains allergens, histamines, antigen epitopes, saline (e.g. for negative control) or other that will be applied to the patient skin 102 by the at least one prong or needle 304. The at least one prong or needle 304 may be disposed within the reservoir such that the contents of the reservoir maybe soaked into or disposed on an outer surface of the prong or needle 304. In at least one embodiment, the prong or needle 304 may be fluidly connected to the reservoir 302 such that the allergens may be delivered to the patient's skin 102 through the prong or needle 304. In another embodiment, the reservoir 302 may be disposed within the body of the prong or needle 304 such that the allergens may be delivered to the patient's skin 102 by dissolution of the prong or needle after initial penetration.

The at least one prong or needle 304 may extend from or extend through a first surface 306 of the reservoir 302. The first surface 306 is disposed substantially parallel to and coplanar with the shelf 222 or surface of the capture device 112 while the first applicator 106 is in the first applicator first position, as shown in FIGS. 1 and 4.

The allergens may be delivered to the first predetermined area 300 of the patient's skin 102 while the first applicator 106 is in the first applicator second position, as shown in FIG. 5. The allergens may be delivered to a patient's epidermis by the prong 304 or may be delivered intradermally by the needle 304.

In at least one embodiment, a control prong 308 may be provided with the first applicator 106 and/or the second applicator 108. As shown in FIG. 1, the control prong 308 is provided with the first applicator 106 and is spaced apart from the prong 304. The control prong 308 is not configured to deliver allergens but instead is arranged to prick the patient's skin 102 to provide a negative control or a negative control substance such that engagement of the control prong 308 with the first predetermined area 300 of the patient's skin 102 causes a mechanical injury to determine a patient's baseline response to a prong absent the known allergens. For example, the engagement of the control prong 308 with the first predetermined area 300 of the patient's skin 102 may lead to the formation of a small wheal that may have no or minimal clinical significance. The small wheal may serve as a baseline or a control that is compared by the allergy testing device 100 to a wheal that may form due to the delivery of allergens within the first predetermined area 300 of the patient's skin 102 by the prong 304 of the first applicator 106 and/or a wheal that may form due to the introduction of allergens that are delivered to a second predetermined area 310 of the patient's skin 102 by the second prong 314. The comparison of the control wheal or small wheal to the wheal enables the allergy testing device 100 to determine the potential clinical significance of the wheal.

The second applicator 108 is spaced apart from the first applicator 106. In the embodiments shown, the second applicator 108 is spaced apart from the first applicator 106 by the protrusion 220. The second applicator 108 is arranged to apply antigen epitopes or the like to a second predetermined area 310 of the patient's skin 102, as shown in FIGS. 2, 3, and 5. The second predetermined area 310 is spaced apart from the first predetermined area 300. A footprint of or a cross sectional area of the second applicator 108 may be equal to or less than the second predetermined area 310.

The second applicator 108 includes a reservoir 312 and a prong or a needle 314. The reservoir 312 contains allergens, histamines, antigen epitopes, saline (e.g. for negative control) or the like that will be applied to the patient skin 102 by the at least one prong or needle 314. The at least one prong or needle 314 may be disposed within the reservoir such that the contents of the reservoir maybe soaked into or disposed on an outer surface of the prong or needle 314. In at least one embodiment, the prong or needle 314 may be fluidly connected to the reservoir 312 such that the antigen epitopes may be delivered to the patient's skin 102 through the prong or needle 314. In another embodiment, the reservoir 312 may be disposed within the body of the prong or needle 314 such that the allergens may be delivered to the patient's skin 102 by dissolution of the prong or needle after initial penetration.

The at least one prong or needle 314 may extend from or extend through a second surface 316 of the reservoir 312. The second surface 316 is disposed substantially parallel to and coplanar with the shelf 222 or surface of the capture device 112 while the second applicator 108 is in the second applicator first position, as shown in FIGS. 1 and 4.

The antigen epitopes may be delivered or applied to the second predetermined area 310 of the patient's skin 102 while the second applicator 108 is in the second applicator second position, as shown in FIG. 5. The antigen epitopes may be delivered to a patient's epidermis by the prong 314 or may be delivered intradermally by the needle 314.

The first applicator 106 and the second applicator 108 are independently moved between their respective first and second positions by the drive device 110. The drive device 110 may be a mechanical system, an electromechanical system, a piezoelectric system, a micromechanical actuator, or a manual actuation system that is substantially disposed within the second housing member 202.

The drive device 110 includes a first guide rail 400, a first actuator 402, a second guide rail 404, and a second actuator, 406. The first guide rail 400 extends between and is connected to the first applicator 106 and the first housing member 200. In such an embodiment, the first applicator 106 and the first guide rail 400 may be integrated members such that both may be discarded after use. In other embodiments, the first guide rail 400 extends between and is connected to the first applicator 106 and the second housing member 202. The first guide rail 400 may be a spring assisted guide rail that is arranged to facilitate the movement of the first applicator 106 between the first applicator first position and the first applicator second position. The spring may be disposed about or provided with the first guide rail 400. The spring is arranged to bias the first applicator 106 towards the first applicator first position.

The first actuator 402 may be an electric motor or geared mechanism having a cam roller, or the like that is engaged with the first guide rail 400 or the first applicator 106. Operation of the first actuator 402 is arranged to move the prong/needle 304 of the first applicator 106 smoothly towards and away from the patient's skin 102.

The second guide rail 404 extends between and is connected to the second applicator 108 and the first housing member 200. In such an embodiment, the second applicator 108 and the second guide rail 404 may be integrated members such that both may be discarded after use. In other embodiments, the second guide rail 404 extends between and is connected to the second applicator 108 and the second housing member 202. The second guide rail 404 may be a spring assisted guide rail that is arranged to facilitate the movement of the second applicator 108 between the second applicator first position and the second applicator second position. The spring be disposed about or provided with the second guide rail 404. The spring is arranged to bias the second applicator 108 towards the second applicator first position.

The second actuator 406 may be an electric motor or geared mechanism having a cam roller, or the like that is engaged with the second guide rail 404 of the second applicator 108. Operation of the second actuator 402 moves the prong/needle 314 of the second applicator 108 smoothly towards and away from the patient's skin 102.

The capture device 112 is disposed within the protrusion 220 of the second housing member 202 of the housing 104. The capture device 112 may extend at least partially through the shelf 222 or may be spaced apart from or extends through an opening defined within the shelf 222.

The capture device 112 includes one or more cameras 500 and a projector 502. The camera 500 has a field of view 504 of the patient's skin 102. The field of view 504 of the camera 500 enables the camera 500 to capture both the first predetermined area 300 and the second predetermined area 310 of the patient's skin 102.

The camera 500 may be an imaging device such as a photo detector or other detector that is arranged to capture or generate one or more images of the first predetermined area 300 and the second predetermined area 310 of the patient's skin 102. In at least one embodiment, the camera 500 is arranged to operate in the visible light spectrum while another embodiments the camera 500 may be arranged to operate in other light spectrums such as ultraviolet, thermal, or the like.

The projector 502 is arranged to project predetermined patterns onto the patient's skin 102 within at least one of the first predetermined area 300 and the second predetermined area 310. The projector 502 includes an illumination source and a grating or pattern generator. The illumination source may emit or transmit selected wavelengths such as ultraviolet radiation, visible radiation, infrared radiation, or the like. Pattern generation may be achieved through any manner of means including, but not limited to, analogue methods, digital spatial light modulation, or laser interference.

Referring to FIG. 3, the projector 502 projects a first predetermined pattern or series of patterns 510 onto the patient's skin 102 within the first predetermined area 300. The projector 502 is also arranged to project a second predetermined pattern or series of patterns 512 onto the patient's skin 102 within the second predetermined area 310.

The set/series of patterns projected by projector 502 onto the patient's skin 102 may consist of alternating bands of at least two different electromagnetic frequencies. The frequency of band alternation may be sequentially modulated and may additionally include phase shifting and/or re-orientation of the projected pattern.

Referring back to FIGS. 1, 4, and 5, the processor 114 may be provided as part of a controller that is disposed within the second housing member 202. The processor 114 is in communication with the drive device 110, the capture device 112, and in some embodiments, the first applicator 106 and the second applicator 108. The processor 114 is configured to execute program instructions maintained on a memory medium. The processor 114 may execute any of the various steps described throughout the present disclosure. Further, the processor 114 may be configured to receive data including, but not limited to, images of the first and second predetermined areas 300, 310 of the patient's skin 102 from the camera 500 of the capture device 112. The processor 114 may also control the indication of a positive or negative test result and may further control a display to monitor testing progress or status.

The processor 114 may include a processing element such as any microprocessor-type device configured to execute algorithms and/or instructions. The term "processor" may be broadly defined to encompass any device having one or more processing elements, which execute program instructions from a non-transitory memory medium. Further, the steps described throughout the present disclosure may be carried out by a single processor/controller or multiple processors/controllers.

The memory medium may include any storage medium known in the art suitable for storing program instructions executable by the processor 114. For example, the memory medium may include a non-transitory memory medium or non-transitory computer readable medium. By way of another example, the memory medium may include, but is not limited to, read-only memory, random access memory, magnetic or optical memory device, magnetic tape, solid state drive, or the like. The memory medium may be housed together with the processor 114. In at least one embodiment, the memory medium may be located remotely with respect to the processor 114. For instance, the processor 114 may access remote memory such as a server that is accessible through a network.

The processor 114 may perform the steps discussed below and shown in conjunction with the flow chart of FIG. 6. The processor 114 may: operate the projector 502 of the capture device 110 to project a first predetermined set/series of patterns 510 onto the patient's skin 102 within the first predetermined area 300 and/or the second predetermined area 310; operate the camera 500 of the capture device 110 to capture a first image set/series of the first predetermined area 300 and/or the second predetermined area 310 of the patient's skin 102; operate the drive device 110 to move the first applicator 106 from the first applicator first position towards the first applicator second position to apply allergens to the patient's skin 102 within the first predetermined area 300; after a predetermined period of time, operate the projector 502 of the capture device 110 to project a second predetermined set/series of patterns 512 onto the patient's skin 102 within the first predetermined area 300; operate the camera 500 of the capture device 110 to capture a second image set/series of the first predetermined area 300 of the patient's skin 102; determine the significance of the second image set/series; operate the drive device 110 to move the second applicator 108 from the second applicator first position towards the second applicator second position to apply allergens or antigen epitopes to the patient's skin 102 within the second predetermined area 310; after a second predetermined period of time, operate the projector 502 of the capture device 110 to project a third predetermined pattern set/series 514 onto the patient's skin 102 within the second predetermined area 310; operate the camera 500 of the capture device 110 to capture a third image set/series of the second predetermined area 310 of the patient's skin 102; determine the clinical significance of the second image set/series; and operate an indicator 520 to output for display whether an allergic reaction has occurred within at least one of the first predetermined area 300 and/or the second predetermined area 310.

Figure 6:
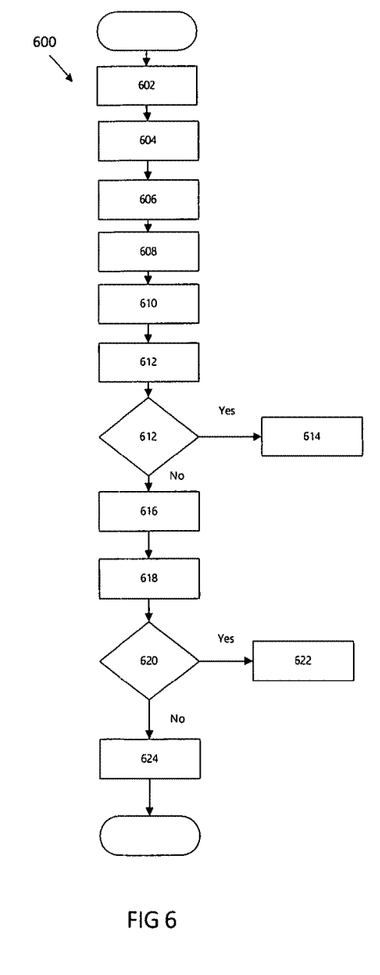
FIG. 6 illustrates a flow diagram depicting a method of allergy testing, in accordance with one or more embodiments of the present disclosure.

FIG. 6 is a flow chart illustrating steps performed in an allergy testing method 600, in accordance with one or more embodiments of the present disclosure. Applicant notes that the embodiments and enabling technologies described previously herein in the context of the allergy testing device 100 should be interpreted to extend to the method 600. It is further noted, however, that the method 600 is not limited to the architecture of the allergy testing device 100.

The method includes positioning the allergy testing device 100 on a body part of a patient, such as the forearm of a patient, at step 602. The allergy testing device 100 is positioned such that the capture device has a clear and unobstructed view of the patient's skin 102. In some embodiments, the method includes an initializing step 604 in which the capture device 112 determines or identifies the first predetermined area 300 and the second predetermined area 310 on the patient's skin. Identifying the first predetermined area 300 and the second predetermined area 310 may include calculating an initial map in cartesian coordinates, a grid, or the like. The initial map or grid will aid the processor to correlate a prong/needle of the first or second applicator 106, 108 to a specific location or region after application of the allergen/antigen epitopes to a patient's skin 102.

The method further includes a first capture step 606 that includes projecting the first series/set of patterns 510 on the patient's skin 102 using the projector 502 and capturing a first set/series of images of the first predetermined area 300 using the camera 500. The first capture step 606 provides an initial or baseline capture of the first predetermined area 300 and in some embodiments may also include capturing a first set/series of images of the second predetermined area 310 of the patient's skin using the projector 502 and camera 500 of the capture device 112.

The method further includes a first application step 608 that includes applying an allergen to the patient's skin 102 within the first predetermined area 300 of the patient's skin 102 with the first applicator 106. The allergen may be applied to the patient's epidermis by a prong or applied intradermally by a needle.

The method further includes a second capture step 610 that includes projecting the second series/set of patterns 512 and capturing a second set/series of images of the first predetermined area 300 of the patient's skin 102 using the projector 502 and camera 500 of the capture device 112 after a first predetermined time period. The first predetermined time period provides a sufficient amount of time for a potential allergic reaction to occur such that a wheal may begin formation within the first predetermined area 300 of the patient's skin 102.

The method further includes a first determination step 612 that may include comparing the first image set/series and the second image set/series to each other. In at least one embodiment, should an allergic reaction occur such that a wheal forms within the first predetermined area 300, the method may assign coordinates, a grid location, or the like to the wheal.

The determination step 612 may be a multistep process that involves first transforming each image set/series from the first capture step 606 and/or the second capture step 610 into a discrete, interpreted object. Transformation of a capture set/series is achieved by signal analysis of the projected and captured patterns visible on the patient's skin 102. The captured pattern in each image of the set/series from the first capture step 606 and/or the second capture step 610, and knowledge of the expected pattern frequency projected in association with each image, are used to calculate the location, size, and features of skin topography of the patient's skin 102 within the first predetermined area 300 which created distortions from the projected pattern's expected appearance. Information about distortions in each image of the set/series is aggregated to generate a three-dimensional point cloud representing the surface of the patient's skin 102. In this way, the entire set/series of the first capture step 606 and/or the second capture step 610 is transformed into a unified point cloud. A series of data cleaning and reconstitution steps are undertaken to optimize the data including correction of natural noise, skin inter-reflections, and subsurface scattering. Anomaly detection is then processed on the generated point cloud to identify changes in skin topography including allergic wheals as well as benign appearances such as nevi, skin tags, and the like. Features of anomalous topography, including size and location, are recorded. These features are further used to perform parametric fitting of the anomalous topography to create interpretations containing objects of interest. If appropriate, the processor 114 compares post-exposure interpretations (those generated from capture set/series collected after operation of the applicators), to baseline interpretations (those generated from capture set/series collected before operation of the applicators) and/or interpretations collected previous to the most recent application step to identify those objects of interest which represent benign skin topography such as nevi, skin tags, and the like or wheals developed in response to previous applications. When indicated, the processor 114 then uses prior knowledge of control substance application position to compare intra-interpretation objects of interest resulting from control substance application to the remaining objects of interest identified as neither benign nor control objects. Finally, the device uses feature information derived from these non-benign, non-control objects, in addition to thresholding information, to determine the clinical significance of the interpretation through feature analysis compared against the threshold.

As understood by one of ordinary skill in the art, clinical significance means that an identifiable wheal has formed or has begun forming such that the skin topography may have changed due an allergic reaction. Clinical significance may be differentiated from non-allergic changes by feature analysis of the identified change compared to the current topography of the patient's skin 102 at the site of negative control substance exposure, e.g. control prong 308. A wheal is considered clinically significant for an allergic sensitivity when it is larger than a wheal induced by the negative control substance by a predetermined threshold. Alternatively, if the negative control substance does not induce a wheal, or if a negative control substance is not applied as part of the test, then a wheal is considered clinically significant for allergic sensitivity when it is simply larger than a predetermined threshold. Current literature and professional guidance recommend a threshold of 3 millimeters.

Should the determination derived from the image set/series be considered significant or to have clinical significance at step 612, the method continues to the first output step 614. The first output step 614 includes outputting for display a first indicator indicative of an allergic reaction via the indicator 520. The first indicator may be an auditory, visual, or other indicator that may be output by the allergy testing device 100. The method may then end If a difference between the first image set/series and the second image set/series is less than the threshold, the method continues to the second application step 616.

The second application step 616 includes applying or delivering allergens or antigen epitopes within the second predetermined area 310 of the patient's skin 102 with the second applicator 108. The allergens or antigen epitopes may be applied to the patient's epidermis by a prong or applied intradermally by a needle.

The method further includes a third capture step 618 that includes projecting the third series/set of patterns 514 on the patient's skin 102 using the projector 502 and capturing a third set/series of images of the second predetermined area 310 using the camera 500 after a second predetermined time period. The second predetermined time period provides a sufficient amount of time for a potential allergic reaction to occur such that a wheal may be formed within the second predetermined area 310 of the patient's skin 102. The second predetermined time period may be substantially equal to the first predetermined time period or may be different from the first predetermined time period.

The method further includes a second determination step 620 that may include comparing the third image set/series to at least one of the first image set/series and the second image set/series. In at least one embodiment, should an allergic reaction occur such that a wheal forms within the second predetermined area 310, the method may assign coordinates, grid location, or the like to the wheal.

Should the determination derived from the third image set/series be considered significant, the method continues to the second output step 622. The second output step 622 includes outputting for display a second indicator indicative of an allergic reaction via the indicator 520. The second indicator may be an auditory, visual, or other indicator that may be output by the allergy testing device 100. If a difference between the third image set/series to at least one of the first image set/series and the second image set/series be less than the threshold, the method may output for display a third indicator indicative of no allergic reaction at 624 via the indicator 520.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The previous description is presented to enable one of ordinary skill in the art to make and use the present disclosure as provided in the context of a particular application and its requirements. As used herein, directional terms such as "left", "right", "top," "bottom," "over," "under," "upper," "upward," "lower," "down," and "downward" are intended to provide relative positions for purposes of description and are not intended to designate an absolute frame of reference. Various modifications to the described embodiments will be apparent to those with skill in the art, and the general principles defined herein may be applied to other embodiments. The present disclosure is not intended to be limited to the particular embodiments shown and described but is to be accorded the widest scope consistent with the principles and novel features herein disclosed.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

All of the methods described herein may include storing results of one or more steps of the method embodiments in memory. The results may include any of the results described herein and may be stored in any manner known in the art. The memory may include any memory described herein or any other suitable storage medium known in the art. After the results have been stored, the results can be accessed in the memory and used by any of the method or system embodiments described herein, formatted for display to a user, used by another software module, method, or system, and the like. Furthermore, the results may be stored "permanently," "semi-permanently," temporarily," or for some period of time. For example, the memory may be random access memory (RAM), and the results may not necessarily persist indefinitely in the memory.

It is further contemplated that each of the embodiments of the method described above may include any other step(s) of any other method(s) described herein and may also be performed in a different order. In addition, each of the embodiments of the method described above may be performed by any of the systems described herein.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to physically able to mate and/or physically interacting components and/or wirelessly interactable and/or wirelessly interacting components and/or logically interacting and/or logically interactable components.

Furthermore, it is to be understood that the present disclosure is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," and the like). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, and the like" is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, and the like). In those instances where a convention analogous to "at least one of A, B, or C, and the like" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, and the like). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. An allergy testing device, comprising: a housing; a first applicator operatively connected to the housing, wherein the first applicator includes at least one prong or needle arranged to apply at least one allergen to a patient's skin; a second applicator operatively connected to the housing and spaced apart from the first applicator, wherein the second applicator includes at least one needle arranged to apply at least one allergen to the patient's skin; a drive device operatively connected to the housing and each of the first applicator and the second applicator, the drive device arranged to move the first applicator between a first applicator first position and a first applicator second position and move the second applicator between a second applicator first position and a second applicator second position, and wherein the first applicator is configured to apply the at least one allergen while in the first applicator second position and the second applicator is configured to apply the at least one allergen while in the second applicator second position; a capture device operatively connected to the housing and spaced apart from the first applicator; and at least one processor in communication with the drive device and the capture device, the processor programmed to: operate the capture device to project a first predetermined set of patterns onto the patient's skin within at least one of a first and second predetermined areas; operate the capture device to capture a first set of images of the at least one of the first and second predetermined areas of the patient's skin; and operate the drive device to move the first applicator from the first applicator first position towards the first applicator second position, within the at least one of the first and second predetermined areas; operate the capture device to project a second predetermined set of patterns onto the patient's skin within the at least one of the first and second predetermined areas; operate the capture device to capture a second set of images of the at least one of the first and second predetermined areas; evaluate the second set of images and render a first determination; operate the drive device to move the second applicator from the second applicator first position towards the second applicator second position, within the second predetermined area in response to the first determination derived from the second set of images being considered clinically insignificant.

2. The allergy testing device of claim 1, wherein the processor is further programmed to:
   operate the capture device to project a third predetermined pattern set on the patient's skin within the at least one of the first and second predetermined areas;
   operate the capture device to capture a third image set of the at least one of the first and second predetermined areas of the patient's skin; and
   evaluate the third image set and render a second determination.

3. The allergy testing device of claim 2, wherein the processor is further programmed to: responsive to the second determination derived from the third image set being considered insignificant, output for display a second indicator, indicative of no allergic response.

* * * * *